United States Patent [19]

Sasse et al.

[11] Patent Number: 4,663,327

[45] Date of Patent: May 5, 1987

[54] 1-HETEROARYL-4-ARYL-PYRAZOLIN-5-ONES

[75] Inventors: Klaus Sasse, Bergisch-Gladbach; Wilhelm Brandes, Leichlingen; Gerd Hänssler, Leverkusen; Paul Reinecke, Leverkusen; Hans-Georg Schmitt, Leverkusen; Wilfried Paulus, Krefeld, all of Fed. Rep. of Germany

[73] Assignee: Bayer Aktiengesellschaft, Leverkusen, Fed. Rep. of Germany

[21] Appl. No.: 733,450

[22] Filed: May 10, 1985

[30] Foreign Application Priority Data

May 23, 1984 [DE] Fed. Rep. of Germany ....... 3419127
Aug. 18, 1984 [DE] Fed. Rep. of Germany ....... 3430433

[51] Int. Cl.$^4$ .................. A61K 31/53; A61K 31/505; A61K 31/44; A01N 43/66; A01N 43/54; A01N 43/40; C07D 401/04; C07D 403/04

[52] U.S. Cl. ..................... 514/275; 540/461; 540/520; 514/212; 514/245; 514/259; 514/260; 514/258; 514/269; 514/273; 514/274; 514/341; 544/207; 544/209; 544/284; 544/253; 544/310; 544/317; 544/321; 544/331; 544/333; 544/324; 544/327; 544/328; 546/279

[58] Field of Search ............... 514/269, 275, 341, 212, 514/245, 259, 260, 258, 273, 274; 546/279; 544/333, 330, 324, 331, 332, 323, 321, 325, 328, 207, 209, 284, 253, 310, 317, 327

[56] References Cited

U.S. PATENT DOCUMENTS 3,758,465  9/1973  Jenkins ................................. 546/279
3,956,339  5/1976  Furutachi et al. ................... 546/279
3,957,814  5/1976  Moller et al. ........................ 546/279
4,482,716  11/1984  Long .................................... 546/279

*Primary Examiner*—John M. Ford

*Attorney, Agent, or Firm*—Sprung Horn Kramer & Woods

[57] ABSTRACT

Microbicidally active novel 1-heteroaryl-4-aryl-pyrazolin-5-ones of the formula

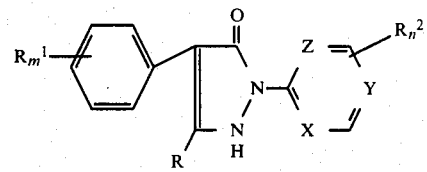

in which R represents hydrogen or alkyl, $R^1$ represents halogen, hydroxyl, optionally substituted alkyl, optionally substituted alkoxy, optionally substituted phenoxy, a radical —$S(O)_p$— alkyl which is optionally substituted in the alkyl part, nitro, optionally substituted amino or a fused-on carbocyclic or heterocyclic radical, p represents an integer 0, 1 or 2, $R^2$ represents halogen or optionally substituted alkyl, or represents alkoxy, alkylmercapto, nitro, cyano, carboxamide or a fused-on carbocyclic radical, m represents an integer from 0 to 5, n represents an integer from 0 to 4, it being possible for the substituents to be identical or different when m and/or n represent a number greater than 1, and X, Y and Z are identical or different and represent a nitrogen atom or the radical =CH or

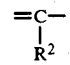

wherein $R^2$ has the meaning given above, with the proviso that at least one of the radicals X, Y and Z denotes a nitrogen atom.

12 Claims, No Drawings

1-HETEROARYL-4-ARYL-PYRAZOLIN-5-ONES

The invention relates to new 1-heteroaryl-4-aryl-pyrazolin-5-ones, a process for their preparation, and their use as microbicides.

It is already known that certain heterocyclic compounds, such as, for example, N-trichloromethylthiophthalimide and -tetrahydrophthalimide, have good fungicidal actions (see U.S. Pat. Nos. 2,553,770, 2,553,771 and 2,553,776). Furthermore, organic sulphur compounds, such as, for example, zinc ethylene-1,2-bis-(dithiocarbamate), are also compounds which have a good fungicidal activity (see, for example, R. Wegler "Chemie der Pflanzenschutz- und Schädlingsbekämpfungsmittel" (Chemistry of Plant Protection Agents and Pest-Combating Agents), Springer Verlag, Berlin, Heidelberg, New York 1970, Volume 2, page 65 et seq.).

Under certain conditions, for example when low amounts and concentrations are used, the action of these compounds will not always be completely satisfactory in some fields of use, for example in the field of plant protection. However, because of insufficient stability in aqueous media, the use of the known compounds for the protection of industrial materials is unsatisfactory.

1,4-Diarylpyrazolin-5-ones are also known, and can be employed as herbicides. Nothing is known concerning microbicidal activity (see DE-OS (German Published Specification) 2,651,008).

New 1-heteroaryl-4-aryl-pyrazolin-5-ones of the formula (I)

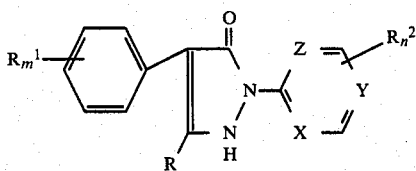

in which
R represents hydrogen or alkyl,
$R^1$ represents halogen, hydroxyl, optionally substituted alkyl, optionally substituted alkoxy, optionally substituted phenoxy, a radical —$S(O)_p$— alkyl which is optionally substituted in the alkyl part, nitro, optionally substituted amino or a fused-on carbocyclic or heterocyclic radical, p represents an integer 0, 1 or 2,
$R^2$ represents halogen or optionally substituted alkyl, or represents alkoxy, alkylmercapto, nitro, cyano, carboxamide or a fused-on carbocyclic radical,
m represents an integer from 0 to 5,
n represents an integer from 0 to 4, it being possible for the substituents to be identical or different when m and/or n represent a number greater than 1, and
X, Y and Z are identical or different and represent a nitrogen atom or the radical =CH or

wherein $R^2$ has the meaning given above, with the proviso that at least one of the substituents X, Y and Z denotes a nitrogen atom,
have been found.

The compounds of the formula (I) can be present in tautomeric equilibrium with the compounds of the formula (IA):

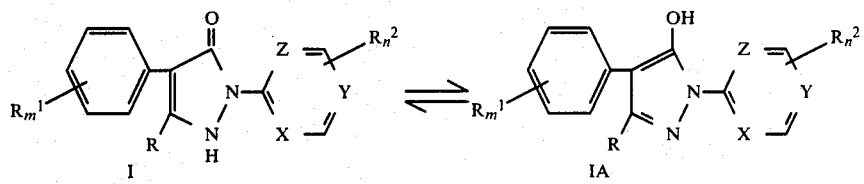

For the sake of simplicity, in the text below reference will always be made to compounds of the formula (I), although both the pure compounds and mixtures of these containing various amounts of the compounds of the formula (I) and (IA) are meant.

Furthermore, it has been found that the new 1-heteroaryl-4-aryl-pyrazolin-5-ones of the formula (I)

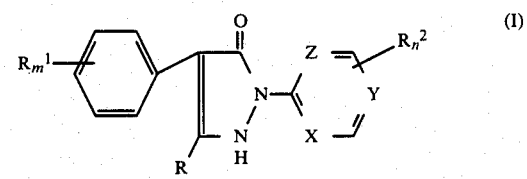

in which
R represents hydrogen or alkyl,
$R^1$ represents halogen, hydroxyl, optionally substituted alkyl, optionally substituted alkoxy, optionally substituted phenoxy, a radical —$S(O)_p$— alkyl which is optionally substituted in the alkyl part, nitro, optionally substituted amino or a fused-on carbocyclic or heterocyclic radical,
p represents an integer 0, 1 or 2,
$R^2$ represents halogen or optionally substituted alkyl, or represents alkoxy, alkylmercapto, nitro, cyano, carboxamide or a fused-on carbocyclic radical,
m represents an integer from 0 to 5,
n represents an integer from 0 to 4, it being possible for the substituents to be identical or different when m and/or n represent a number greater than 1, and
X, Y and Z are identical or different and represent a nitrogen atom or the radical =CH or

wherein $R^2$ has the meaning given above, with the proviso that at least one of the substituents X, Y and Z denotes a nitrogen atom,
are obtained if α-acylphenyl acetates or their derivatives of the formula (II)

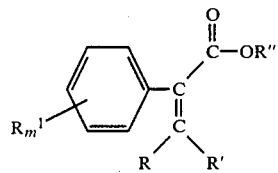

in which

R, R¹ and m have the meanings given above,

R' represents hydroxyl, alkoxy, halogen, dialkylamino or the —O—SO₂R''' group,

R'' represents alkyl or optionally substituted aryl and

R''' represents optionally substituted alkyl, optionally substituted aryl or dialkylamino, are reacted with hydrazinoheterocycles of the formula (III)

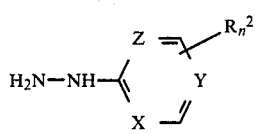

in which X, Y, Z, R² and n have the meanings given above, if appropriate in the presence of a solvent or diluent and, if appropriate, in the presence of a base or acid.

Finally, it has been found that the 1-heteroaryl-4-aryl-pyrazolin-5-ones of the formula (I) can be employed as microbicides.

In this respect, the compounds according to the invention, of the formula (I), surprisingly exhibit a higher and broader microbicidal activity than the microbicidally active compounds previously known from the prior art, such as, for example, N-trichloromethylthiophthalimide or -tetrahydrophthalimide, zinc ethylene-1,2-bis-(dithiocarbamate) and/or N,N-dimethyl-N'-phenyl-N'-dichlorofluoromethylthio-sulphamide. The compounds according to the invention thus represent an enrichment of the art.

Formula (I) gives a general definition of the 1-heteroaryl-4-aryl-pyrazolin-5-ones according to the invention. Preferred compounds of the formula (I) are those
in which R represents hydrogen or alkyl having 1 to 4 carbon atoms, R¹ represents halogen, hydroxyl, alkyl having 1 to 4 carbon atoms, halogenoalkyl having 1 or 2 carbon atoms and 1 to 5 identical or different halogen atoms, alkoxy having 1 to 6 carbon atoms, halogenoalkoxy having 1 or 2 carbons and 1 to 5 identical or different halogen atoms, alkoxyalkoxy having 1 to 4 carbon atoms per alkyl part, alkylthioalkoxy having 1 to 4 carbon atoms per alkyl part, aryloxyalkoxy having 1 to 4 carbon atoms in the alkyl part and 6 to 10 carbon atoms in the aryl part, phenoxy which is optionally monosubstituted to polysubstituted by identical or different substituents, alkylthio having 1 to 6 carbon atoms, halogenoalkylthio having 1 or 2 carbon atoms and 1 to 5 identical or different halogen atoms, alkoxyalkylthio having 1 to 4 carbon atoms per alkyl part, alkylthioalkylthio having 1 to 4 carbon atoms per alkyl part, alkylsulphinyl having 1 to 6 carbon atoms, halogenoalkylsulsulphinyl having 1 or 2 carbon atoms and 1 to 5 identical or different halogen atoms, alkoxyalkylsulphinyl or alkylthioalkylsulphinyl having 1 to 4 carbon atoms per alkyl part, alkylsulphonyl having 1 to 6 carbon atoms, halogenoalkylsulphonyl having 1 or 2 carbon atoms and 1 to 5 identical or different halogen atoms, alkoxyalkylsulphonyl or alkylthioalkylsulphonyl having 1 to 4 carbon atoms per alkyl part, nitro, amino, mono- or dialkylamino having 1 to 4 carbon atoms per alkyl part, acylamino having 1 to 4 carbon atoms or a fused-on 5-membered or 6-membered carbocyclic ring which can be interrupted by one atom, or more than one identical or different atoms, from amongst oxygen, sulphur and nitrogen, R² represents halogen, alkyl having 1 to 4 carbon atoms, halogenoalkyl having 1 or 2 carbon atoms and 1 to 5 identical or different halogen atoms, alkoxyalkyl or alkylthioalkyl having 1 to 4 carbon atoms per alkyl part, alkoxy having 1 to 4 carbon atoms, alkylthio having 1 to 4 carbon atoms, nitro, cyano, carboxamide or a fused-on carbocyclic ring, m represents an integer from 0 to 3, n represents an integer from 0 to 3, and X, Y and Z are identical or different and represent a nitrogen atom or the radical =CH— or

wherein R² has the meaning given above, with the proviso that at least one of the radicals X, Y and Z denotes a nitrogen atom.

Particularly preferred compounds of the formula (I) are those
in which

R represents hydrogen, methyl or ethyl,

R¹ represents fluorine, chlorine, bromine, methyl, ethyl, n-propyl, isopropyl, trifluoromethyl, dichlorofluoromethyl, methoxy, ethoxy, n-propoxy, isopropoxy, trifluoromethoxy, dichlorofluoromethoxy, methoxymethoxy, ethylthiomethoxy, 1-methylthioethoxy, 2-ethylthio-ethoxy, phenoxymethoxy, phenoxy, methylthio, ethylthio, trifluoromethylthio, dichlorofluoromethylthio, methoxymethylthio, ethoxymethylthio, methylthiomethylthio, methylsulphinyl, ethylsulphinyl, methylsulphonyl, nitro, cyano, amino, methylamino, ethylamino, dimethylamino, diethylamino, acetamino, a fused-on benzene ring or a fused-on 5-membered or 6-membered heterocyclic structure which has 1 or 2 oxygen atoms and is optionally monosubstituted or polysubstituted by fluorine, R² represents fluorine, chlorine, bromine, methyl, ethyl, n-propyl, isopropyl, tert.-butyl, trifluoromethyl, dichlorofluoromethyl, methoxymethyl, ethoxymethyl, methylthiomethyl, methoxy, ethoxy, n-propoxy, isopropoxy, methylthio, ethylthio, nitro, cyano, carboxamide or a fused-on benzene ring, m represents an integer from 0 to 3, n represents an integer from 0 to 3, it being possible for the substituents to be identical or different when m and/or n represent a number greater than 1, and X, Y and Z are identical or different and represent a nitrogen atom or the radical =CH— or

wherein R² has the meaning given previously, with the proviso that one of the radicals X, Y and Z denotes a nitrogen atom.

Very particularly preferred compounds of the formula (I) are those
in which
R represents hydrogen, methyl or ethyl,
R¹ represents fluorine, chlorine, bromine, methyl, ethyl, trifluoromethyl, methoxy, ethoxy, trifluoromethoxy, phenoxy, methylthio, ethylthio, trifluoromethylthio, nitro, cyano, amino, dimethylamino, acetamido, a fused-on benzene ring or a fused-on 5-membered heterocyclic structure which has 2 oxygen atoms and is polysubstituted by fluorine,
R² represents fluorine, chlorine, bromine, methyl, ethyl, tert.-butyl, trifluoromethyl, methoxy, methylthio, nitro, cyano, carboxamide or a fused-on benzene ring,
m represents an integer from 0 to 3,
n represents an integer from 0 to 3, and
X represents a nitrogen atom, and
Y and Z represent the radical =CH— or

or
Y represents a nitrogen atom and
X and Z represent the radical =CH— or

or
X and Z each represent a nitrogen atom and
Y represents the radical =CH— or

or
X and Y each represent a nitrogen atom and
Z represents the radical =CH— or

If, for example, ethyl α-hydroxymethylene-phenylacetate and 2-hydrazino-pyrimidine are used as starting materials, the course of the reaction can be represented by the following equation:

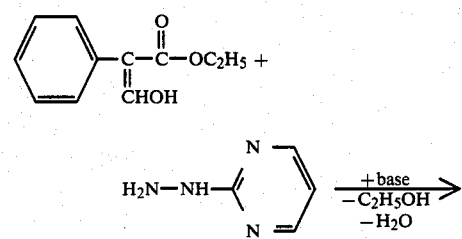

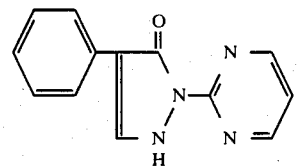

Formula (II) gives a general definition of the α-acylphenylacetates or their derivatives which are to be used as starting materials in carrying out the process according to the invention. In this formula, R, R¹ and m have the meaning which have already been mentioned for the substituents in connection with the description of substances according to the invention, of the formula (I).

In this formula,
R' preferably represents hydroxyl, alkoxy having 1 to 3 carbon atoms, chlorine, bromine, dimethylamino, methylsulphonyloxy, trifluoromethylsulphonyloxy or phenylsulphonyloxy and
R" preferably represents alkyl having 1 to 3 carbon atoms or optionally nitro-substituted phenyl.

The α-acylphenylacetates or their derivatives of the formula (II) are known in principle. If one or other of the compounds should still be unknown, it can be prepared analogously to the methods below.

In the case in which R represents a hydrogen atom, this compound is obtained from appropriately substituted alkyl phenylacetates by reaction with a formic acid derivative. Thus, compounds II in which R' represents hydroxyl are prepared by the action of methyl or ethyl formate in the presence of strong bases, such as alkali metal alcoholates, sodium amide or the like (see, for example, B. 20, 2931 (1887); B. 28, 771 (1895); and Ann. 291, 164 (1896)), the compounds first formed being the alkali metal salts (II; R'=O-metal), which can also be employed directly in the subsequent reaction or are converted, by treatment with aqueous acids, to the free hydroxymethylene compounds, which are in tautomeric equilibrium with the corresponding α-formylphenylacetates.

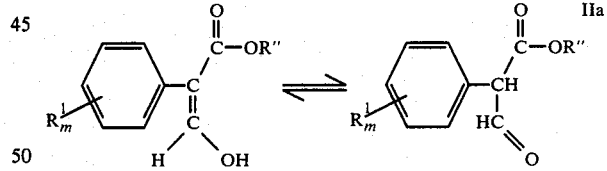

Compounds in which R'=OAlk are prepared, as described in the literature, by the action of alkylating agents on compounds II in which R'=OH, under basic conditions (see, for example, Ann. 424, 228 (1921); J. Chem. Soc. 1953, 3548; J. org. Chem. 45, 2576 (1980)), or by etherification of the same compounds with alcohols in the presence of p-toluene-sulphonic acid (see, for example, J. Chem. Soc. 1953, 3548).

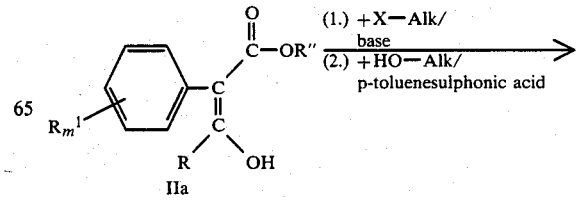

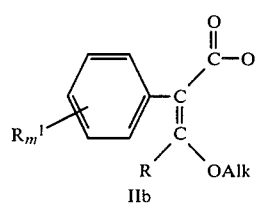
IIb

Compounds II in which R′=a R‴—SO₂—O group can be prepared from the corresponding compounds II in which R′=OH by reaction with sulphonyl chlorides, such as methanesulphonyl chloride, trifluoromethanesulphonyl chloride or p-toluenesulphonyl chloride, in the presence of alkalis:

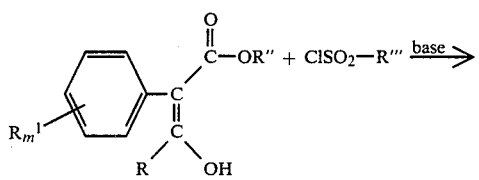
IIc

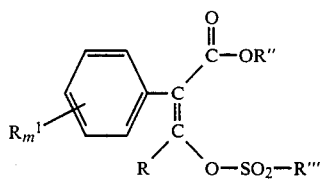

Compounds II in which R′=Hal are obtained by reacting the hydroxymethylene compounds (II) in which R′=OH with inorganic acid chlorides, preferably phosphorus(V) chloride (see, for example, B. 51, 1366 (1918)).

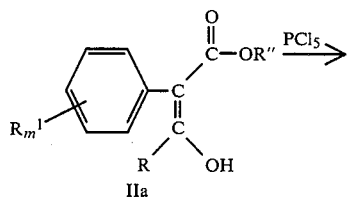
IIa

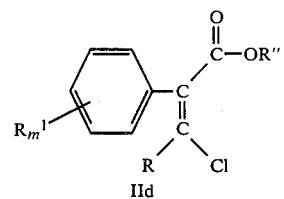
IId

Compounds II in which R′=dialkylamino are obtained by reacting the appropriately substituted alkyl phenylacetates with dialkylformamide dialkyl acetals (see Tetrahedron Lett. 16, 1361 (1979)), for example

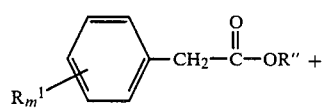

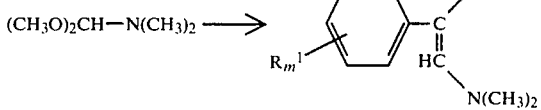
IIe

Another method for the preparation of these compounds (II e) comprises the reaction of the hydroxymethylene derivatives (II a) with secondary amines (see A. ch. [10] 18, 103, 114 (1932)).

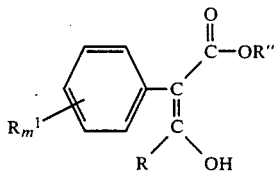
IIa

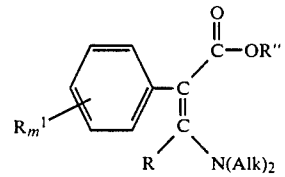
IIe

In principle, the same methods can be used for the preparation of the compounds of the formula II, in which R represents a lower alkyl radical, as are used for the preparation of the compounds in which R=hydrogen, although these methods give inadequate yields. The synthesis of these compounds takes place with higher yields when the acylation is carried out not for the phenylacetates but with phenylacetonitrile, and the nitrile group is subsequently converted to the ester group:

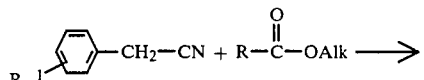

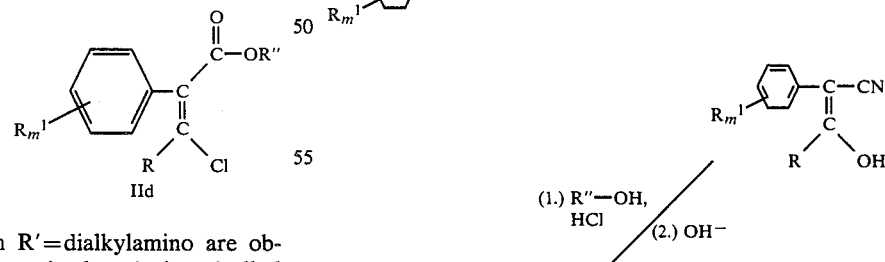

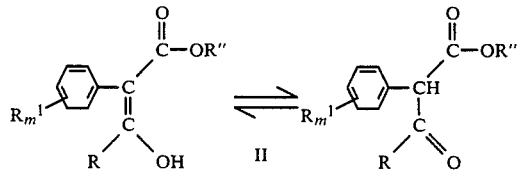
II

The precursors of the formula III which are furthermore required for the preparation of the compounds according to the invention, of the formula I, are invariably known. They are hydrazinopyridines, hydrazinopyrimidines, hydrazino-1,3,5-triazines and the corresponding compounds with fused-on rings:

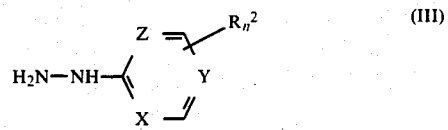
(III)

In this formula X, Y, Z, $R^2$ and n have the meaning which have already been mentioned for these substituents in connection with the description of substances according to the invention, of the formula (I).

The preparation of the compounds III is known in principle. Variants of III which have not been described to date can be prepared by analogous method, in particular (a) by reaction of halogeno-N-heterocycles or alkoxy- or alkylmercapto-N-heterocycles with hydrazine:

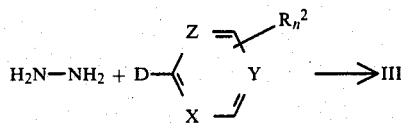

D=Hal, OAlk, SAlk or (b) by reduction of heterocyclic diazonium compounds:

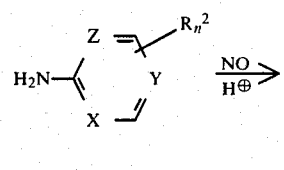

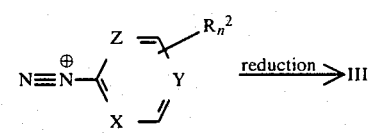

or (c) by reduction of heterocyclic nitramino compounds:

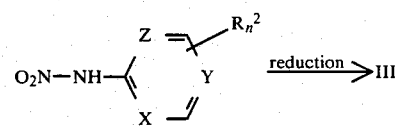

The following may be mentioned as examples of intermediate products of the formula III:

| | m.p. (°C.)/b.p. | References |
|---|---|---|
| 2-Hydrazino-pyridine | b.p.$_{12}$:130 | J. Chem. Soc. 107, 691 (1915) |
| 5-Chloro-2-hydrazino-pyridine | 127–128 | |
| 6-Chloro-2-hydrazino-pyridine | 116–117 | |
| 3,5-Dichloro-2-hydrazino-pyridine | 172–174 | |
| 5-Bromo-2-hydrazino-pyridine | 133–134 | |
| 3-Nitro-2-hydrazino-pyridine | 200 | B. 57, 1192 (1924) |
| 5-Nitro-2-hydrazino-pyridine | 204 (decomposition) | E.P. 2,471,488 |
| 5-Cyano-2-hydrazino-pyridine | 185–186 | |
| 2-Hydrazino-4-methyl-pyridine | 74–75 | Ann. 656, 103 (1962) |
| 2-Hydrazino-6-methyl-pyridine | HCl salt: 194 (decomposition) | |
| 4-Chloro-2-hydrazino-6-methyl-pyridine | 162–163 | |
| 3-Nitro-2-hydrazino-6-methyl-pyridine | 138–139 | J. am. Chem. Soc. 74, 3828 (1952) |
| 5-Nitro-2-hydrazino-6-methyl-pyridine | 119–121 | |
| 2-Hydrazino-4,6-dimethyl-pyridine | | |
| 3-Cyano-2-hydrazino-6-methyl-pyridine | 243 (decomposition) | |
| 2-Hydrazine-5-trifluoromethyl-pyridine | 68–69 | |
| 4-Hydrazino-pyridine | b.p.$_{18}$:187 | B. 59, 317 (1926) |
| 4-Hydrazino-2,6-dimethyl-pyridine | | B. 31, 2497 (1898) |
| 3-Chloro-4-hydrazino-pyridine | | |
| 2-Hydrazino-quinoline | 142–143 | J. Chem. Soc. 103, 1978 (1913) |
| 2-Hydrazino-4-methyl-quinoline | 145–146 | |
| 4-Hydrazino-quinoline | | |
| 1-Hydrazino-isoquinoline | 172 | Ann. 656, 103 (1962) |
| 2-Hydrazino-pyrimidine | 110–111 | |
| 5-Fluoro-2-hydrazino-pyrimidine | 140–141 | |
| 5-Chloro-2-hydrazino-pyrimidine | 183–184 | |
| 4-Methoxy-2-hydrazino-pyrimidine | | |
| 2-Hydrazino-4-methyl-pyrimidine | 85–86 | |
| 2-Hydrazino-4,6-dimethyl-pyrimidine | 165 | J. chem. Soc. 1952, 4691 |
| 4-Methoxy-2-hydrazino-6-methyl-pyrimidine | | |
| 4-Hydrazino-pyrimidine | | |
| 4-Hydrazino-5-methyl-pyrimidine | 205–206 | Bl. Soc. chim. Belg. 68, 30, 32 (1959) |
| 4-Hydrazino-6-methyl-pyrimidine | 140–141 | B. 34, 1241 (1901) |

| | m.p. (°C.)/b.p. | References |
|---|---|---|
| 4-Hydrazino-2,6-dimethyl-pyrimidine | 192–193 | Bl. Soc. chim. Belg. 68, 30, 32 (1959) |
| 6-Chloro-4-hydrazino-2-methyl-pyrimidine | 152 (decomposition) | |
| 1-Methoxy-4-hydrazino-6-methyl-pyrimidine | | |
| 5-Methoxy-4-hydrazino-2-methyl-pyrimidine | | |
| 5-Methoxy-4-hydrazino-2-tert.-butyl-pyrimidine | 213–214 | |
| 2-Methylmercapto-4-hydrazino-pyrimidine | 143–144 | |
| 2-Methylmercapto-4-hydrazino-6-methyl-pyrimidine | 142–143 | |
| 2-Hydrazino-4,6-dimethyl-1,3,5-triazine | | |
| 4-Methoxy-2-hydrazino-6-methyl-1,3,5-triazine | | |
| 4-Methylmercapto-2-hydrazino-6-methyl-1,3,5-triazine | | |
| 4,6-Dimethoxy-2-hydrazino-1,3,5-triazine | 121 | |

The reaction of the substituted atropates of the formula (II) with the hydrazino-N-heterocycles of the formula (III) to give the 1-heteroaryl-4-aryl-pyrazolin-5-ones according to the invention, of the formula (I), takes place in two stages, in that first the terminal amino group of the heterocyclic hydrazine reacts with the enol, enamine or halogenovinyl group in II to give the ene-hydrazines or hydrazones Ia, and then ring closure takes place to give I, with elimination of the alcohol bonded in II:

zine or toluene, halogeno-hydrocarbons, such as di-, tri- and tetrachloromethane, alcohols, such as methanol, ethanol and isopropanol, ethers, such as diethyl ether, tetrahydrofuran or dioxane, and dimethyl sulphoxide, tetrahydrothiophene dioxide and dimethylformamide. The reactions can also be carried out in water or in mixtures of the stated solvents with water.

The reaction temperatures can be varied within a relatively wide range. In general, the reaction is carried out at between about 0° and 100° C., preferably between

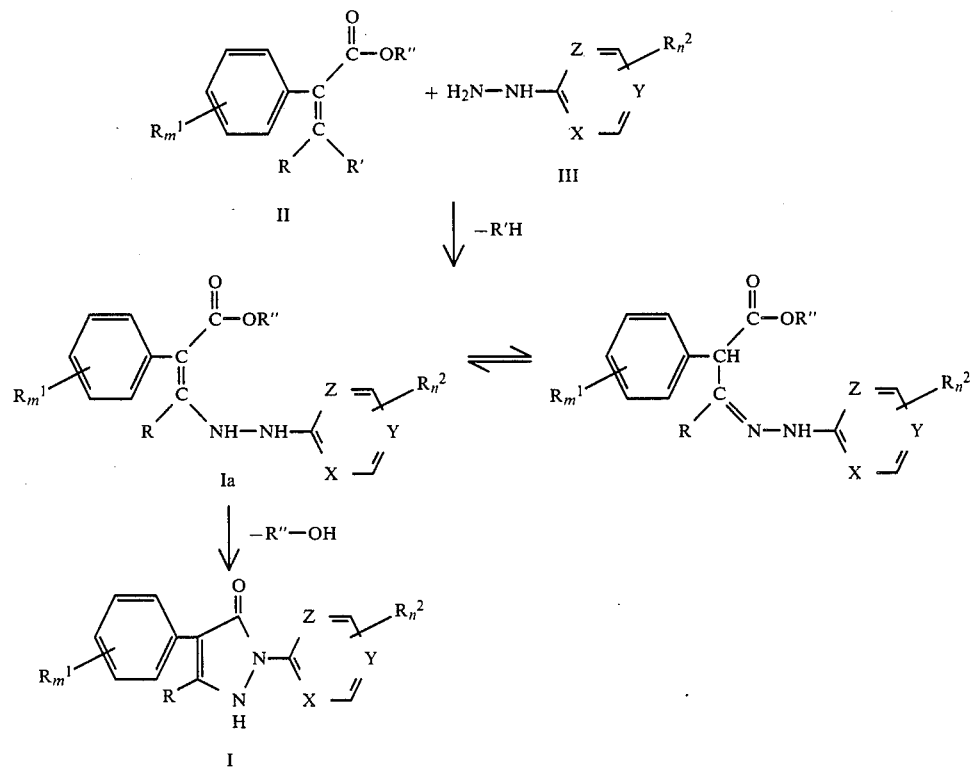

The intermediate products Ia can be isolated and employed in pure form in subsequent reaction. Advantageously, however, both stages are carried out simultaneously or in succession in the same batch.

The reaction of the precursors II and III with one another to give the compounds according to the invention, of the formula I, can be carried out in the absence of a solvent, by heating the components to temperatures between 50° and 150° C.

Advantageously, the reactions are carried out in diluents, and all solvents which are inert to the reactants can be used. These include hydrocarbons, such as benroom temperature and the boiling point of the solvent used.

In many cases, the compounds I are formed from II and III under the stated conditions without further additives. However, depending on the leaving group R' in II, it is frequently advisable to carry out the reaction with the addition of bases or acids. The addition of bases is advantageous when R' represents a leaving group which gives an acid, for example a halogen atom, as in IId, or an R'''—SO$_2$—O group, as in IIc. In these cases, an equimolar amount of a base is preferably used. Suitable bases are alkali metal and alkaline earth metal hydroxides and carbonates, alcoholates or tertiary amines, such as, for example, triethylamine and pyridine.

The addition of acids is advantageous when the leaving group R' constitutes a leaving group which gives a base, for example a dialkylamino group, as in IIe. In these cases, it is preferable to use an equimolar amount of an acid, for example mineral acids, such as hydrochloric acid or sulphuric acid, or an organic acid, such as acetic acid. The following procedure may also be adopted: the enamines IIb are converted to a salt by treatment with an equimolar amount of dry hydrogen chloride in inert solvents, and the salt is employed.

The procedure in an acidic medium can, however, also be advantageous when compounds of the formula II in which R'=OH (IIa) or R'=OAlk are used, as a rule submolar amounts of 0.1 to 0.2 mol being sufficient. Instead of adding the acid subsequently, it is, hovver, also possible to proceed in such a way that the hydrazinoheterocycles of the formula III are introduced into the reaction not as free bases but in the form of their salts, for example the hydrochlorides.

This procedure is advisable particularly when the hydrazines, such as 2-hydrazino-pyridine and 4-hydrazinopyridine, tend to decompose in the form of free bases.

When the procedure is carried out in an acidic medium, the reaction stops, as a rule, at the uncyclized stage Ia. For ring closure to give the compounds I according to the invention, a neutral, advantageously basic medium is required. If the first stage of the reaction is carried out in an acidic medium, it is therefore necessary to add a base. Preferred bases are: alkali metal and alkaline earth metal hydroxides, carbonates and alcoholates, and alkali metal amides (preferably when the procedure is carried out in an anhydrous medium).

The base is used in an amount which is at least equivalent to the amount of acid. An excess up to 1 mol more can be advantageous, but the medium should have a pH value of at least 9. The cyclization stage (Ia→I) is carried out a temperature between 0° C. and the boiling point of the solvent used, preferably between 5° and 100° C.

In an alkaline medium, oxidizable intermediate products occur, which can be detected by a yellow to violet coloration. Hence, it is advisable to carry out the cyclization reaction in a basic medium in an inert gas atmosphere, for example under nitrogen.

The compounds according to the invention, of the formula I, form salt-like compounds with bases. As a rule, working-up of the reaction mixtures is therefore carried out so that, before isolation of the reaction products, an amount of an acid, for example hydrochloric acid, sulphuric acid or acetic acid, which is at least equivalent to the amount of the base employed is added. The following procedure may also be adopted: the alkali metal or alkaline earth metal salts, which as a rule are precipitated from the reaction medium, are removed from the reaction mixture by filtration, or filtration under suction, and subsequently treated with at least an equivalent amount of an aqueous acid.

The active compounds according to the invention exhibit a powerful microbicidal action and can be employed in practice for combating undesired micro-organisms. The active compounds are suitable, inter alia, for use as plant protection agents, especially fungicides, and also as active compounds for combating micro-organisms in industrial materials.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which fall under the generic names listed above may be mentioned as examples, but without imposing any restrictions:

Botrytis species, such as, for example, *Botrytis cinerea;*
Plasmopara species, such as, for example, *Plasmopara viticola,*
Uromyces species, such as, for example, *Uromyces appendiculatus;*
Sphaerotheca species, such as, for example, *Sphaerotheca fuliginea;*
Venturia species, such as, for example, *Venturia inaequalis;*
Podosphaera species, such as, for example, *Podosphaera leucotricha;*
Phytophthora species, such as, for example, *Phytophthora infestans;*
Erysiphe species, such as, for example, *Erysiphe graminis;*
Puccinia species, such as, for example, *Puccinia recondita;*
Fusarium species, such as, for example, *Fusarium culmorum;*
Ustilago species, such as, for example, *Ustilago nuda* or *avenae,*
Septoria species, such as, for example, *Septoria nodorum;*
Tilletia species, such as, for example, *Tilletia caries;*
Pyricularia species, such as, for example, *Pyricularia oryzae;*
Pellicularia species, such as, for example, *Pellicularia sasakii;*
Pyrenophora species, such as, for example, *Pyrenophora teres* (conidia form: Drechslera, Syn: Helminthosporium);
Leptosphaeria species, such as, for example, *Leptosphaeria nodorum;*
Cochliobolus species, such as, for example, *Cochliobolus sativus;* (conidia form; Drechslera, Syn: Helminthosporium) and
Cerospora species, such as, for example, *Cercospora canescens.*

The good toleration by plants of the active compounds at the concentrations required for combating plant diseases permits treatment of the above-ground parts of plants, of vegetative propagation and seeds, and of the soil.

As plant protection agents, the active compounds according to the invention can be used with particularly good success for combating fruit and vegetable diseases, such as, for example, against the late blight of tomato causative organism (*Phytophthora infestants*) and the grey mould of beans causative organism (*Botrytis cinerea); additionally besides for combating rice diseases, such as for example, against the rice blast causative organism (Pyricularia oryzae),* and furthermore for combating cerveal diseases, for example those caused by *Leptosphaeria nodorum, Cochliobolus sativus* and *Drechslera graminea.* Furthermore, fungicidal action against powdery mildew fungi on cucumber and cereals and cereals, against apple scab, and against rust and *Pyrenophora teres* on cereal may be mentioned. The bactericidal action of the compounds may also be mentioned.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicates acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, emulsions, foams, suspensions, wettable powders, pastes and soluble powders, dusting agents and granules. They are used in the customary manner, for example by watering, spraying, atomizing, scattering, dusting, foaming, brushing on etc. It is also possible to apply the active compounds by the ultra low volume method, or to inject the preparation of active compound or the active compound itself into the soil. It is also possible to treat the seed of the plants.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The 1-heteroaryl-4-aryl-pyrazolin-5-ones according to the invention can, as already mentioned, also be used as active compounds for combating microorganisms in industrial materials.

According to the invention, industrial materials are innate materials which have been prepared for use in industry. For example, industrial materials which are to be protected by active compounds according to the invention for microbial modification or destruction can be adhesives, glues, paper and cardboard, textiles, leather, wood, paints and plastic articles, cooling lubricants and other materials which can be infested or destroyed by microorganisms. Parts of production plants, for example cooling water cycles adversely affected by multiplication of microorganisms, may also be mentioned within the range of the materials to be protected. Adhesives, papers, leather, wood, paints, cooling lurbicants, textiles and plastics may preferably be mentioned as industrial materials within the scope of the present invention.

Examples of microorganisms which can effect degradation or modification of the industrial materials are bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:
Alternaria, such as *Alternaria tenuis*,
Aspergillus, such as *Aspergillus niger*,
Chaetomium, such as *Chaetomium globosum*,
Coniophora, such as *Coniophora puteana*,
Lentinus, such as *Lentinus trigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeroginosa* and
Staphylococcus, such as *Staphylococcus aureus*.

Depending on the field of use, the active compound according to the invention can be converted to the customary formulations, such as solutions, emulsions, suspensions, powders, pastes and granules.

These can be prepared in a manner which is in itself known, for example by mixing the active compounds with an extender which consists of a liquid solvent and/or solid carriers, if appropriate with the use of surface-active agents, such as emulsifiers and/or dispersing agents, and, in the case of the use of water as an extender, organic solvents, such as alcohols, can, if appropriate, be used as auxiliaries.

Liquid solvents for the active compounds can be, for example, water, alcohols, such as lower aliphatic alcohols, preferably ethanol or isopropanol, or benzyl alcohol, ketones, such as acetone or methyl ethyl ketone, liquid hydrocarbons, such as petroleum fractions, and halogenated hydrocarbons, such as 1,2-dichloroethane.

Microbicidal agents for the protection of industrial materials contain the active compounds in general in an amount of from 1 to 95%, preferably from 10 to 75%.

The use concentrations of the active compound according to the invention depend on the type and occurrence of the microorganisms to be combated, and on the composition of the material to be protected. The optimum use amount can be determined by test series. In general, the use concentrations are in the range from 0.001 to 5% by weight, preferably from 0.05 to 1.0% by weight, relative to the material to be protected.

The active compounds according to the invention can also be present as a mixture with other known active compounds. The following active compounds may be mentioned as examples: benzyl alcohol mono(poly)-hemiformal and other compounds which eliminate formaldehyde, benzimidazolyl methylcarbamates, tetramethylthiuram disulphide, zinc salts of dialkyl dithiocarbamates, 2,4,5,6-tetrachloroisophthalodinitrile, thiazolylbenzimidazole, mercaptobenzothiazole, organo-tin compounds, methylene bisthiocyanate, and phenol derivatives, such as 2-phenylphenol, (2,2'-dihydroxy-5,5'-dichloro)-diphenylmethane and 3-methyl-4-chloro-phenol.

PREPARATION EXAMPLES

Example 1

Variant 1a:

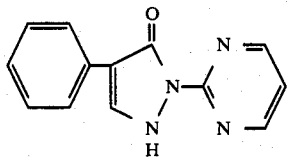

19.2 g (0.1 mol) of ethyl α-hydroxymethylene-phenylacetate and 11 g (0.1 mol) of 2-hydrazino-pyrimidine in 150 ml of ethanol are boiled under reflux for 3 hours. The mixture is cooled to room temperature, and 9 g (0.1 mol) of concentrated sodium hydroxide solution are then added dropwise, while stirring. Stirring is then continued for 2 hours at room temperature, and the mixture is then boiled under reflux for 2 hours. The mixture is neutralized with concentrated hydrochloric acid, and diluted with 1 l of water. The precipitated crystals are filtered off under suction and dried in the air. 15 g (63% of theory) of 1-pyrimid-2-yl-4-phenyl-pyrazolin-5-one of melting point 159° to 160° C. (from ethanol) are obtained.

Variant 1b:

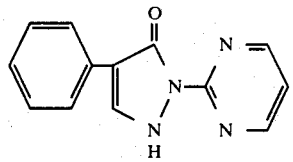

20.6 g (0.1 mol) of ethyl α-methoxymethylene-phenylacetate (b.p.$_{0.2}$: 103° to 106° C.) are boiled under reflux with 11 g (0.1 mol) of 2-hydrazino-pyrimidine in 100 ml of dioxane for 24 hours. The solvent is distilled off in vacuo, and the residue is stirred in 50 ml of toluene. During this procedure, 3.2 g (13.5% of theory) of 1-pyrimid-2-yl-4-phenyl-pyrazolin-5-one separate out, and are filtered off under suction and dried. They have a melting point of 159° to 160° C. (from ethanol).

Variant 1c:

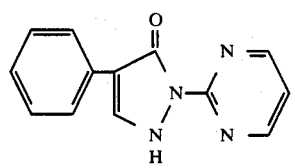

19.2 g (0.1 mol) of ethyl α-hydroxymethylene-phenylacetate are dissolved in 100 ml of acetonitrile, and first 11.2 g (0.1 mol) of potassium tert.-butylate are added, after which 19 g (0.1 mol) of p-toluenesulphonyl chloride are added in portions at 20° to 25° C. The mixture is stirred for 4 hours at room temperature and left to stand overnight. The precipitated salt is filtered off under suction, and the filtrate is evaporated down in vacuo. The residue is dissolved in toluene, and the solution is washed with water, dried over sodium sulphate and evaporated down in vacuo. 23 g (73% of theory) of ethyl α-(4-methyl-phenylsulphonyloxymethylene)-phenylacetate are obtained. The oil is dissolved in 150 ml of ethanol, and then 7.7 g (0.07 mol) of 2-hydrazino-pyrimidine are added. The mixture is stirred for 10 hours at room temperature, and then 13.5 g of concentrated sodium hydroxide solution are added dropwise in the course of 4 hours. After stirring has been continued for a further 5 hours at room temperature, dilute hydrochloric acid is added dropwise until the neutral point is reached, and the mixture is diluted with 750 ml of water. The oily product which separates out is taken up in a small amount of ether, 3.6 g (22% of theory) of 1-pyrimid-2-yl-4-phenylpyrazolin-5-one being precipitated. Melting point 159° to 160° C. (from ethanol).

Example 2

Variant 2a:

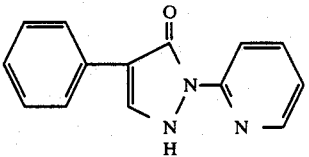

22.7 g (0.1 mol) of the potassium salt of ethyl α-hydroxymethylene-phenylacetate and 18.2 g (0.1 mol) of 2-hydrazino-pyridine dihydrochloride in 200 ml of ethanol are stirred for 30 minutes at room temperature and then boiled under reflux for 5 hours. After the mixture has been cooled to room temperature, 19.1 g (1.7 mol) of potassium tert.-butylate are introduced in portions while nitrogen is simultaneously passed over the mixture. The mixture is stirred for 4 hours at room temperature and left to stand overnight. The precipitate formed is filtered off under suction and suspended in 100 ml of water, and the suspension is slightly acidified with acetic acid. The crystals are filtered off under suction, washed with water and dried in the air. 17.2 g (72.5% of theory) of 1-pyrid-2-yl-4-phenyl-pyrazoline-5-one of melting point 132° to 133° C. (ethanol) are obtained.

Variant 2b:

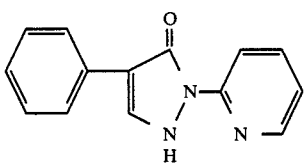

21.2 g (0.1 mol) of phenyl phenylacetate are heated with 11.9 g (0.1 mol) of dimethylformamide dimethyl acetal to 100° C. for 5 hours. All volatile components are then distilled off at this temperature in a vacuum from a water pump. The residue, which essentially consists of phenyl α-dimethylaminomethylene-phenylacetate, is dissolved in 100 ml of ethanol without further purification, 18.2 g (0.1 mol) of 2-hydrazinopyridine dihydrochloride are added to the solution, and the mixture is boiled under reflux for 5 hours. After the mixture has been cooled, 6.4 g (27% of theory) of reaction product separate out. This product is filtered off under suction and dried. 18.2 g (0.16 mol) of potassium tert.-butylate are added in portions to the remaining ethanolic solution, at room temperature and under nitrogen. After the mixture has been stirred for 5 hours at room temperature, the precipitate is filtered off under suction and suspended in 100 ml of water, and the suspension is acidified with acetic acid. The crystals are filtered off under suction, washed with water and dried in the air. A further 8.2 g of reaction product are obtained. The total yield of 1-pyrid-2-yl-4-phenyl-pyrazolin-5-one is 14.6 g (61.6% of theory).

EXAMPLE 3

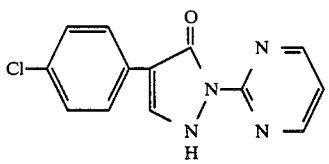

19.9 g (0.1 mol) of ethyl 4-chloro-phenylacetate are heated with 23.8 g (0.2 mol) of dimethylformamide dimethyl acetal to 100° C. for 5 hours. All volatile components are then distilled off at this temperature in a vacuum from a water pump. The oily residue, which essentially consists of ethyl α-dimethylaminomethylene-4-chlorophenylacetate, is dissolved in 140 ml of ethanol without further purification, and 11 g (0.1 mol) of 2-hydrazinopyrimidine and 10 ml of concentrated hydrochloric acid are added. The mixture is heated under reflux for 5 hours and cooled to room temperature, and, after the addition of 9 g of concentrated sodium hydroxide solution, is stirred for 5 hours at room temperature. After it has been neutralized with dilute hydrochloric acid, the mixture is diluted with 1 l of water. The precipitated crystals are filtered off under suction, washed with water and dried in the air. 7.2 g (26.4% of theory) of 1-pyrimid-2-yl-4-(4-chlorophenyl)-pyrazolin-5-one of melting point 190° to 191° C. (methanol) are obtained.

The compounds below can be prepared by the methods described above. For recrystallization, the following solvents were used, these being referred to in each case in the last column of the table below:

a: ethanol
b: butanol
c: toluene
d: methanol
e: ethyl acetate
f: dioxane
g: cleaner's naphtha
h: dimethylformamide
i: glycol monomethyl ether

TABLE 1

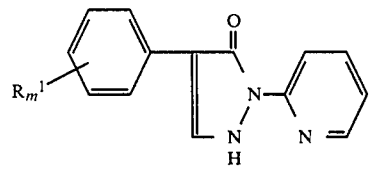

| Example No. | $R^1$ | m | Melting point (°C.) | Recrystallization from |
|---|---|---|---|---|
| 4 | — | 0 | 131–133 | a |
| 5 | 2-F | 1 | 128–130 | g |
| 6 | 4-F | 1 | 137–139 | a |
| 7 | 2-Cl | 1 | 109–111 | a |
| 8 | 3-Cl | 1 | 146–147 | a |
| 9 | 4-Cl | 1 | 175–177 | b |
| 10 | 2-Br | 1 | 108 | b |
| 11 | 2-F, 6-Cl | 2 | 167–168 | b |
| 12 | 2,4-Cl$_2$ | 2 | 168–169 | b |
| 13 | 3,4-Cl$_2$ | 2 | 184–185 | b |
| 14 | 2-OCH$_3$ | 1 | 110–112 | a |
| 15 | 4-OCH$_3$ | 1 | 104–106 | a |
| 16 | 3-OC$_6$H$_5$ | 1 | 148–149 | b |
| 17 | 3-OCF$_3$ | 1 | 114–116 | a |
| 18 | 4-OCF$_3$ | 1 | 120–122 | g |
| 19 | 4-SCF$_3$ | 1 | 186–188 | a |
| 20 | —O—CF$_2$—O— (3,4-position) | 2 | 179–181 | c |
| 21 | 2-CH$_3$ | 1 | 86–88 | b |
| 22 | 3-CH$_3$ | 1 | 154–156 | a |
| 23 | 4-CH$_3$ | 1 | 132–133 | a |
| 24 | 3-CF$_3$ | 1 | 130–131 | a |
| 25 | 4-CF$_3$ | 1 | 171–173 | b |
| 26 | 2-Cl, 5-CF$_3$ | 2 | 116–118 | g |
| 27 | 3-CF$_3$, 4-Cl | 2 | 204–206 | b |
| 28 | 3,5-(CF$_3$)$_2$ | 2 | 174–176 | c |
| 29 | —CH=CH—CH=CH— (2,3-position) | 2 | 146 | a |
| 30 | 4-OC$_2$H$_5$ | 1 | 122 | a |
| 31 | 4-OC$_3$H$_7$—n | 1 | 114–116 | a |
| 32 | 3,5-(CH$_3$)$_2$ | 2 | 150–152 | a |
| 33 | 4-NH—CO—CH$_3$ | 1 | 203–205 | f |

TABLE 2

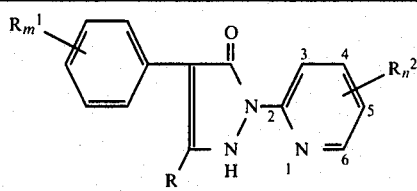

| Example No. | R¹ | m | R | R² | n | Melting point (°C.) | Recrystallization from |
|---|---|---|---|---|---|---|---|
| 34 | — | 0 | $CH_3$ | — | 0 | 114–116 | a |
| 35 | — | 0 | $C_2H_5$ | — | 0 | 72–73 | g |
| 36 | — | 0 | H | 6-Cl | 1 | 155–157 | b |
| 37 | 2-F, 6-Cl | 2 | H | 6-Cl | 1 | 220–221 | f |
| 38 | 3,4-$Cl_2$ | 2 | H | 6-Cl | 1 | 207 | f |
| 39 | 4-$CF_3$ | 1 | H | 6-Cl | 1 | 160–161 | b |
| 40 | — | 0 | H | 5-Cl | 1 | 209–211 | f |
| 41 | 2-Cl | 1 | H | 5-Cl | 1 | 195–197 | b |
| 42 | 3,4-$Cl_2$ | 2 | H | 5-Cl | 1 | 210–211 | b |
| 43 | 2-$OCH_3$ | 1 | H | 5-Cl | 1 | 176–177 | b |
| 44 | 2-$CH_3$ | 1 | H | 5-Cl | 1 | 188–190 | b |
| 45 | 3-$CH_3$ | 1 | H | 5-Cl | 1 | 156–158 | b |
| 46 | 4-$CH_3$ | 1 | H | 5-Cl | 1 | 207 | b |
| 47 | 4-$CF_3$ | 1 | H | 5-Cl | 1 | 218–220 | f |
| 48 | — | 0 | $CH_3$ | 5-Cl | 1 | 156–157 | g |
| 49 | — | 0 | H | 5-Cl | 1 | 164–166 | a |
| 50 | 2-Cl | 1 | H | 3,5-$Cl_2$ | 2 | 198–199 | a |
| 51 | 3,4-$Cl_2$ | 2 | H | 3,5-$Cl_2$ | 2 | 112–114 | f |
| 52 | 2-$CH_3$ | 1 | H | 3,5-$Cl_2$ | 2 | 164–166 | c |
| 53 | 2-$OCH_3$ | 1 | H | 5-Br | 1 | 184–186 | b |
| 54 | — | 0 | H | 5-$NO_2$ | 1 | 264 (decomposition) | f |
| 55 | 4-$CH_3$ | 1 | H | 5-$NO_2$ | 1 | 267–268 | h |
| 56 | 4-$CF_3$ | 1 | H | 5-$NO_2$ | 1 | 196–198 | i and d |
| 57 | — | 0 | H | 6-$CH_3$ | 1 | 110–112 | g |
| 58 | — | 0 | H | 4-$CH_3$ | 1 | 171–173 | b |
| 59 | — | 0 | H | 4,6-$(CH_3)_2$ | 2 | 147–149 | g |
| 60 | — | 0 | H | 4-Cl, 6-$CH_3$ | 2 | 214–216 | a |
| 61 | 4-$CF_3$ | 1 | H | 4-Cl, 6-$CH_3$ | 2 | 208–210 | a |
| 62 | — | 0 | H | 5-$CF_3$ | 1 | 172–174 | a |
| 63 | — | 0 | H | 5-CN | 1 | 243–245 | b |
| 64 | — | 0 | H | 3-CN, 6-$CH_3$ | 2 | 300 | a |
| 65 | 2-Cl | 1 | H | 5-CO—$NH_2$ | 1 | 270 | h |
| 66 | — | 0 | H | —CH=CH—CH=CH—; 4-$CH_3$ (5,6-position) | 3 | 180–182 | b |
| 67 | 3,4-$Cl_2$ | 2 | H | —CH=CH—CH=CH—; 4-$CH_3$ (5,6-position) | 3 | 228–230 | f |
| 68 | 4-$CH_3$ | 1 | H | —CH=CH—CH=CH—; 4-$CH_3$ (5,6-position) | 3 | 196 | b |
| 69 | 4-$CF_3$ | 1 | H | —CH=CH—CH=CH—; 4-$CH_3$ (5,6-position) | 3 | 252–254 | b |
| 70 | 4-$OCH_3$ | 1 | —$CH_3$ | — | 0 | 126–128 | g |
| 71 | 2-F | 1 | —$CH_3$ | — | 0 | 98–100 | g |
| 72 | 4-$OCH_3$ | 1 | —$CH_3$ | 5-Cl | 1 | 180–181 | c |
| 73 | 4-$CH_3$ | 1 | —$CH_3$ | — | 0 | 114–115 | g |
| 74 | 3,4-$(Cl)_2$ | 2 | —$CH_3$ | — | 0 | 128–130 | g |
| 75 | 4-$OCH_3$ | 1 | H | 5-Cl | 1 | 167–169 | c |
| 76 | — | 0 | —$CH_3$ | 4-$CH_3$ | 1 | 144–145 | g |
| 77 | 4-$OCH_3$ | 1 | H | 4-$CH_3$ | 1 | 146–148 | g |

TABLE 3

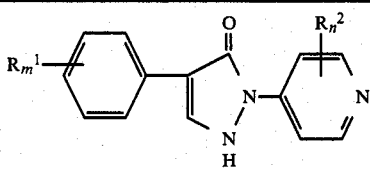

| Example No. | R¹ | m | R² | n | Melting point (°C.) | Recrystallization from |
|---|---|---|---|---|---|---|
| 78 | — | 0 | — | 0 | 242–246 | i |
| 79 | — | 0 | 2,6-$(CH_3)_2$ | 2 | 254 | i |

TABLE 3-continued

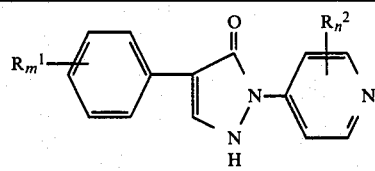

| Example No. | R¹ | m | R² | n | Melting point (°C.) | Recrystallization from |
|---|---|---|---|---|---|---|
| 80 | 4-$CF_3$ | 1 | 2,6-$(CH_3)_2$ | 2 | 260–264 | b |

TABLE 4

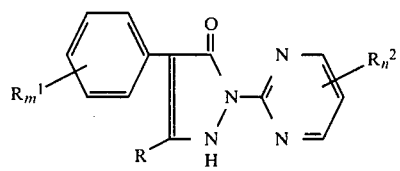

| Example No. | R¹ | m | R | R² | n | Melting point (°C.) | Recrystallization from |
|---|---|---|---|---|---|---|---|
| 81 | — | 0 | H | — | 0 | 158–160 | a |
| 82 | 2-F | 1 | H | — | 0 | 168–170 | a |
| 83 | 4-F | 1 | H | — | 0 | 210–212 | a |
| 84 | 2-Cl | 1 | H | — | 0 | 140–150 | a |
| 85 | 4-Cl | 1 | H | — | 0 | 190–191 | d |
| 86 | 2-Br | 1 | H | — | 0 | 137–138 | a |
| 87 | 2-F, 6-Cl | 2 | H | — | 0 | 178 | b |
| 88 | 2,4-Cl₂ | 2 | H | — | 0 | 243–244 | b |
| 89 | 3,4-Cl₂ | 2 | H | — | 0 | 246–247 | f |
| 90 | 2-OCH₃ | 1 | H | — | 0 | 130 | a |
| 91 | 4-OCH₃ | 1 | H | — | 0 | 166–168 | c |
| 92 | 3-OCF₃ | 1 | H | — | 0 | 162–164 | c |
| 93 | 4-OCF₃ | 1 | H | — | 0 | 170–172 | a |
| 94 | 4-SCF₃ | 1 | H | — | 0 | 202–204 | b |
| 95 | —O—CF₂—O— (3,4-position) | 2 | H | — | 0 | 230–231 | f |
| 96 | 2-CH₃ | 1 | H | — | 0 | 133–134 | b |
| 97 | 3-CH₃ | 1 | H | — | 0 | 156–158 | a |
| 98 | 4-CH₃ | 1 | H | — | 0 | 168–170 | a |
| 99 | 3-CF₃ | 1 | H | — | 0 | 180–181 | b |
| 100 | 4-CF₃ | 1 | H | — | 0 | 226 | b |
| 101 | 2-CF₃, 4-Cl | 2 | H | — | 0 | 150–152 | a |
| 102 | 2-Cl; 5-CF₃ | 2 | H | — | 0 | 182–184 | c |
| 103 | 3-CF₃; 4-Cl | 2 | H | — | 0 | 188–189 | a |
| 104 | 3,5-(CF₃)₂ | 2 | H | — | 0 | 188–189 | a |
| 105 | —CH=CH—CH=CH— (2,3-position) | 2 | H | — | 0 | 146–148 | b |
| 106 | — | 0 | CH₃ | — | 0 | 202–204 | b |
| 107 | — | 0 | H | 5-F | 1 | 245–246 | f |
| 108 | — | 0 | H | 5-Cl | 1 | 267–268 | i |
| 109 | 2-Cl | 1 | H | 5-Cl | 1 | 216–218 | b |
| 110 | 3,4-Cl₂ | 2 | H | 5-Cl | 1 | 242–244 | f |
| 111 | 2-CH₃ | 1 | H | 5-Cl | 1 | 204 | b |
| 112 | 4-CH₃ | 1 | H | 5-Cl | 1 | 264 | b |
| 113 | 4-CF₃ | 1 | H | 5-Cl | 1 | 268–270 | f |
| 114 | — | 0 | H | 6-CH₃ | 1 | 204–206 | a |
| 115 | — | 0 | H | 4,6-(CH₃)₂ | 2 | 256 | c |
| 116 | 4-F | 1 | H | 4,6-(CH₃)₂ | 2 | 275 | b |
| 117 | 4-Cl | 1 | H | 4,6-(CH₃)₂ | 2 | >270 | h |
| 118 | — | 0 | CH₃ | 4,6-(CH₃)₂ | 2 | 181–182 | c |
| 119 | 4-OC₂H₅ | 1 | H | — | 0 | 191–193 | b |
| 120 | 3,5-(CH₃)₂ | 2 | H | — | 0 | 110–112 | e |

TABLE 5

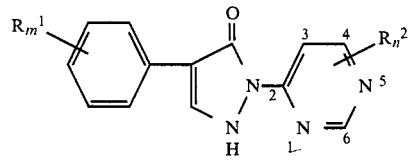

| Example No. | R¹ | m | R² | n | Melting point (°C.) | Recrystallization from |
|---|---|---|---|---|---|---|
| 121 | — | 0 | 4,6-(CH₃)₂ | 2 | 192 | b |
| 122 | 4-CF₃ | 1 | 4,6-(CH₃)₂ | 2 | 196–198 | i |
| 123 | — | 0 | 4-Cl, 6-CH₃ | 2 | 162–164 | g |
| 124 | — | 0 | 3-OCH₃, 6-t-C₄H₉ | 2 | 175 | b |
| 125 | 3,4-Cl₂ | 2 | 3-OCH₃, 6-t-C₄H₉ | 2 | 196–197 | b |
| 126 | 4-CF₃ | 1 | 3-OCH₃, 6-t-C₄H₉ | 2 | 200 | b |
| 127 | — | 0 | 4-CH₃, 6-SCH₃ | 2 | 180–182 | c |
| 128 | 4-CF₃ | 1 | 4-CH₃, 6-SCH₃ | 2 | 174–176 | g |

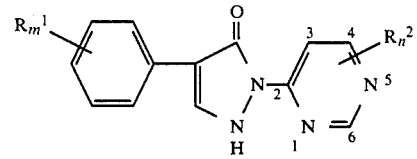

USE EXAMPLES

In the Use Examples below, the compounds listed below are employed as comparative substances:

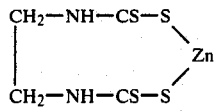

Zinc ethylene-1,2-bis-(dithiocarbamate)

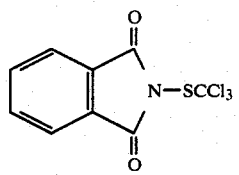

N-Trichloromethylthio-phthalimide

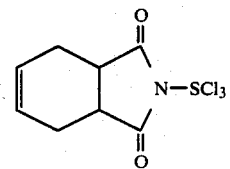

N-Trichloromethylthio-tetrahydrophthalimide

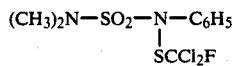

N,N-Dimethyl-N'-phenyl-N'-dichlorofluoromethylthiosulphamide

Example A

Phytophthora Test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabinet at 100% relative atmospheric humidity and at about 20 C.

Evaluation is carried out 3 days after the inoculation.

In this test, a clearly superior activity compared with the prior art is shown, for example, by the compounds according to the following preparation examples: 100, 13, 105, 102, 93 and 92.

Example B

Botrytis test (BEAN)/protective
Solvent: 4.7 parts by weight of acetone
Emulsifier: 0.3 parts by weight alkyl aryl polyglycol ether To produce a suitable preparation of active compound, 1 pat by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compounds according to the following preparation examples: 84, 89, 11, 87, 12, 88, 96, 111, 21, 94 and 102.

Example C

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 80, 122, 25, 68, 84, 105, 28, 11, 7, 102 and 104.

Example D

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 105, 97, 18, 21, 102 and 94.

Example E

Leptosphaeria nodorum test (wheat)/protective
Solvent: 100 parts by weight of dimethylformamide Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 19, 24, 5, 9, 26, 28, 15, 18, 81, 106 and 100.

Example F

*Cochliobolus sativus* test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following preparation examples: 12, 21, 24, 5, 9, 26, 18, 28, 100, 92, 85.

Example G

*Drechslera graminea* test (barley)/seed treatment (syn. *Helminthosporium gramineum*)

The active compounds are used as dry dressings. These are prepared by extending the paticular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptons of stripe disease.

In this test, a clearly superior activity compared with the prior art is shown, for example, by the compound according to the following preparation example: 21.

Example H

To demonstrate the activity against fungi, the minimum inhibitory concentrations (MIC) of active compounds according to the invention are determined:

Active compounds according to the invention are added, in concentrations of 0.1 mg/l to 5,000 mg/l, to an agar prepared from malt extract and peptone. After the agar has solidified, it is contaminated with pure cultures of the test organisms listed in the table. After storage for 2 weeks at 28° C. and 60 to 70% relative atmospheric humidity, the MIC is determined. The MIC is the lowest concentration of active compound at which the microbe species used exhibits no growth at all; it is given in the table below.

TABLE 1

| | MIC's in mg/l for the action of substances according to the invention on fungi | | | | | | | | | | | | | |
|---|---|---|---|---|---|---|---|---|---|---|---|---|---|---|
| Test organisms | according to Example 4 | 5 | 15 | 21 | 23 | 81 | 83 | 84 | 85 | 86 | 90 | 91 | 97 | 100 |
| *Alternaria tenuis* | 50 | 20 | 50 | 10 | 75 | 75 | 50 | 50 | 50 | 20 | 75 | 100 | 50 | 50 |
| *Aspergillus niger* | 7.5 | 3.5 | 20 | 7.5 | 7.5 | 10 | 15 | 10 | 5 | 10 | 35 | 50 | 10 | 500 |
| *Aureobasidium pullulans* | 100 | 20 | 50 | 35 | 50 | 50 | 50 | 20 | 50 | 20 | 75 | 150 | 50 | 50 |
| *Chaetomium globosum* | 1.5 | 0.5 | 0.5 | 0.75 | 0.5 | 3.5 | 3.5 | 1.5 | 1 | 1 | 15 | 20 | 1 | 1 |
| *Coniophora puteana* | 5 | 2 | 5 | 5 | 35 | 0.5 | 5 | 2 | 3.5 | 5 | 5 | 5 | 2 | 5 |
| *Lentinus tigrinus* | 75 | 20 | 50 | 50 | 75 | 5 | 50 | 50 | 7.5 | 2 | 100 | 100 | 10 | 15 |
| *Penicillium glaucum* | 10 | 5 | 75 | 7.5 | 5 | 50 | 20 | 20 | 10 | 50 | 35 | 10 | 10 | 10 |
| *Polyporus versicolor* | 35 | 7.5 | 20 | 7.5 | 3.5 | 2 | 35 | 35 | 5 | 2 | 10 | 20 | 5 | 5 |
| *Sclerophoma pityophila* | 10 | 15 | 50 | 35 | 20 | 7.5 | 5 | 10 | 20 | 10 | 15 | 15 | 20 | 20 |
| *Trichoderma viride* | 200 | 35 | 1000 | 50 | 1000 | 75 | 75 | 35 | 100 | 35 | 150 | 200 | 75 | 500 |

Example J (Action against slime organisms)

Substances according to the invention, dissolved in a small amount of acetone, are used in concentrations of, in each case, 0.1 to 100 mg/l in Allen's nutrient solution (Arch. Mikrobiol. 17, 34 to 53 (1952)), which contains, in 4 l of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam. Shortly beforehand, the nutrient solution is infected with slime organisms (approx. $10^6$ organisms/ml) which have been isolated from the spinning water circulations used in the manufacture of polyamide. Nutrient solutions which have the minimum inhibitory concentration (MIC) or higher concentrations of active compound are still completely clear after culture for three weeks at room temperature, that is to say the pronounced multiplication of the microbes and slime formation, which are noticeable after 3 to 4 days in nutrient solutions which are free of active compound, does not take place.

TABLE

| MIC values in mg/l for the action of the substances stated below on slime organisms | |
|---|---|
| Active compound according to Example | MIC in mg/l |
| 4 | 15 |
| 23 | 7.5 |
| 83 | 35 |

It will be understood that the specification and examples are illustrative but not limitative of the present invention and that other embodiments within the spirit and scope of the invention will suggest themselves to those skilled in the art.

We claim:

1. A 1-heteroaryl-4-aryl-pyrazolin-5-one of the formula

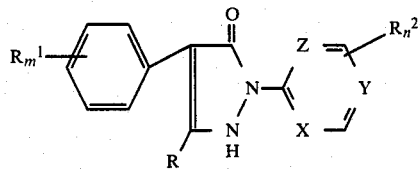

in which

R represents hydrogen or alkyl having 1 to 4 carbon atoms, $R^1$ represents halogen, hydroxyl, alkyl having 1 to 4 carbon atoms, halogenoalkyl having 1 or 2 carbon atoms and 1 to 5 identical or different halogen atoms, alkoxy having 1 to 6 carbon atoms, halogenoalkoxy having 1 or 2 carbons and 1 to 5 identical or different halogen atoms, alkoxyalkoxy having 1 to 4 carbon atoms per alkyl part, alkylthioalkoxy having 1 to 4 carbon atoms per alkyl part, aryloxyalkoxy having 1 to 4 carbon atoms in the alkyl part and 6 to 10 carbon atoms in the aryl part, phenoxy, alkylthio having 1 to 6 carbon atoms, halogenoalkylthio having 1 or 2 carbon atoms and 1 to 5 identical or different halogen atoms, alkoxyalkylthio having 1 to 4 carbon atoms per alkyl part, alkylthioalkylthio having 1 to 4 carbon atoms per alkyl part, alkylsulphinyl having 1 to 6 carbon atoms, halogenoalkylsulsulphinyl having 1 or 2 carbon atoms and 1 to 5 identical or different halogen atoms, alkoxyalkylsulphinyl or alkylthioalkylsulphinyl having 1 to 4 carbon atoms per alkyl part, alkylsulphonyl having 1 to 6 carbon atoms, halogenoalkylsulphonyl having 1 or 2 carbon atoms and 1 to 5 identical or different halogen atoms, alkoxyalkylsulphonyl or alkylthioalkylsulphonyl having 1 to 4 carbon atoms per alkyl part, nitro, amino, mono- or dialkylamino having 1 to 4 carbon atoms per alkyl part, acylamino having 1 to 4 carbon atoms, or two ortho $R^1$ radicals together form a fused-on benzene ring or a fused-on 5-membered or 6-membered heterocyclic structure which has 1 or 2 oxygen atoms and is optionally monosubstituted or polysubstituted by fluorine, $R^2$ represents halogen, alkyl having 1 to 4 carbon atoms, halogenoalkyl having 1 or 2 carbon atoms and 1 to 5 identical or different halogen atoms, alkoxyalkyl or alkylthioalkyl having 1 to 4 carbon atoms per alkyl part, alkoxy having 1 to 4 carbon atoms, alkylthio having 1 to 4 carbon atoms, nitro, cyano, carboxamide or two $R^2$'s together form a fused-on carbocyclic ring, m represents an integer from 0 to 3, n represents an integer from 0 to 3, and X, Y and Z each independently is a nitrogen atom, or the radical

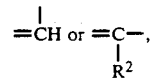

with the proviso that at least one of X, Y and Z is a nitrogen atom.

2. A 1-heteroaryl-4-aryl-pyrazolin-5-one according to claim 1, in which

R represents hydrogen, methyl or ethyl, $R^1$ represents fluorine, chlorine, bromine, methyl, ethyl, n-propyl, isopropyl, trifluoromethyl, dichlorofluoromethyl, methoxy, ethoxy, n-propoxy, isopropoxy, trifluoromethoxy, dichlorofluoromethoxy, methylthiomethoxy, ethylthiomethoxy, 1-methylthioethoxy, 2-ethylthio-ethoxy, phenoxymethoxy, phenoxy, methylthio, ethylthio, trifluoromethylthio, dichlorofluoromethylthio, methoxymethylthio, ethoxymethylthio, methylthiomethylthio, methylsulphinyl, ethylsulphinyl, methylsulphonyl, nitro, cyano, amino, methylamino, ethylamino, dimethylamino, diethylamino, acetamino, or two ortho $R^1$ radicals together form a fused-on benzene ring or a fused-on 5-membered or 6membered heterocyclic structure which has 1 or 2 oxygen atoms and is optionally monosubstituted or polysubstituted by fluorine, and $R^2$ represents fluorine, chlorine, bromine, methyl, ethyl, n-propyl, isopropyl, tert.-butyl, trifluoromethyl, dichlorofluoromethyl, methoxymethyl, ethoxymethyl, methylthiomethyl, methoxy, ethoxy, n-propoxy, isopropoxy, methylthio, ethylthio, nitro, cyano, carboxamide or two $R^2$'s together form a fused-on benzene ring.

3. A 1-heteroaryl-4-aryl-pyrazolin-5-one according to claim 1, wherein such compound is 1-pyridin-2-yl-4-(4-trifluoromethoxyphenyl)-pyrazolin-5-one of the formula

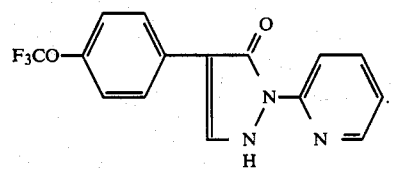

4. A 1-heteroaryl-4-aryl-pyrazolin-5-one according to claim 1, wherein such compound is 4-(2-methylphenyl)-1-pyridin-2-yl-pyrazolin-5-one of the formula

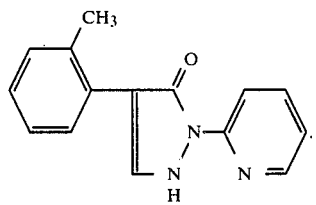

5. A 1-heteroaryl-4-aryl-pyrazolin-5-one according to claim 1, wherein such compound is 4-(3,5-bis-trifluoromethyl-phenyl)-1-pyridine-2-yl-pyrazolin-5-one of the formula

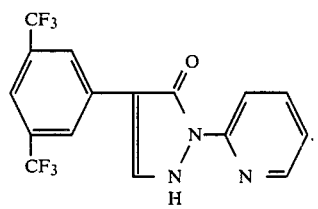

6. A 1-heteroaryl-4-aryl-pyrazolin-5-one according to claim 1, wherein such compound is 4-(2-chlorophenyl)-1-pyrimidin-2-yl-pyrazolin-5-one of the formula

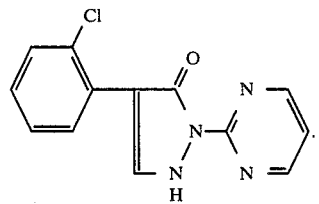

7. A 1-heteroaryl-4-aryl-pyrazolin-5-one according to claim 1, wherein such compound is 4-(2-chloro-6-fluorophenyl)-1-pyrimidin-2-yl-pyrazolin-5-one of the formula

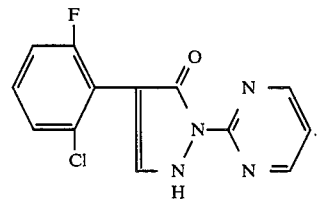

8. A 1-heteroaryl-4-aryl-pyrazolin-5-one according to claim 1, wherein such compound is 4-(2-methoxyphenyl)-1-pyrimidin-2-yl-pyrazolin-5-one of the formula

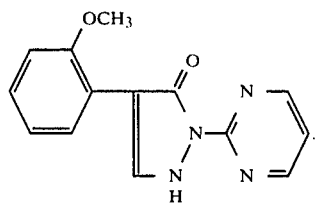

9. A 1-heteroaryl-4-aryl-pyrazolin-5-one according to claim 1, wherein such compound is 1-pyrimidin-2-yl-4-(4-trifluoromethylthiophenyl)-pyrazolin-5-one of the formula

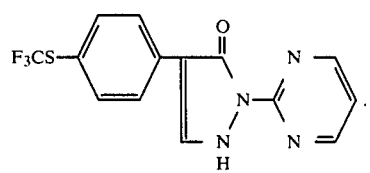

10. A microbicidal or fungicidal composition comprising a microbicidally or fungicidally effective amount of a compound according to claim 1 in admixture with a diluent.

11. A method of combating microbes or fungi which comprises applying to such microbes, fungi, or to a microbe or fungus habitat a microbicidally or fungicidally effective amount of a compound according to claim 1.

12. The method according to claim 11 wherein such compound is
1-pyridin-2-yl-4-(4-trifluoromethoxyphenyl)pyrazolin-5-one,
4-(2-methylphenyl)-1-pyridin-2-yl-pyrazolin-5-one,
4-(3,5-bis-trifluoromethyl-phenyl)-1-pyridine-2-yl-pyrazolin-5-one,
4-(2-chlorophenyl)-1-pyrimidin-2-yl-pyrazolin-5-one,
4-(2-chloro-6-fluoro-phenyl)-1-pyrimidin-2-yl-pyrazolin-5-one,
4-(2-methoxyphenyl)-1-pyrimidin-2-yl-pyrazolin-5-one or
1-pyrimidin-2-yl-4-(4-trifluoromethylthiophenyl)-pyrazolin-5-one.

* * * * *